United States Patent [19]
Sachse

[11] Patent Number: 5,817,122
[45] Date of Patent: Oct. 6, 1998

[54] APPARATUS HAVING A URETER SPLINT AND A GUIDE CONNECTABLE TO THE SPLINT VIA A SCREW CONNECTION, AND HAVING AN AUXILIARY SPLINT

[76] Inventor: Hans E. Sachse, Lerchenstrasse 55, 90425 Nuernberg, Germany

[21] Appl. No.: 674,575

[22] Filed: Jun. 28, 1996

[51] Int. Cl.[6] .................................................. A61B 17/00
[52] U.S. Cl. ............................................................ 606/191
[58] Field of Search ...................................... 606/191, 197, 606/198; 604/39, 57, 104, 109

[56] References Cited

U.S. PATENT DOCUMENTS

| 319,296 | 6/1885 | Molesworth | 606/198 |
|---|---|---|---|
| 876,775 | 1/1908 | Crittenden | 606/191 |
| 1,327,786 | 1/1920 | Stephan | 606/197 |
| 3,908,637 | 9/1975 | Doroshow | 606/191 |
| 5,108,413 | 4/1992 | Moyers | 606/191 |

Primary Examiner—Michael Powell Buiz
Assistant Examiner—William Lewis
Attorney, Agent, or Firm—Keil & Weinkauf

[57] ABSTRACT

The invention is based on an arrangement of a ureter split, a guide and an auxiliary splint, wherein a releasable connection between the guide and the hollow ureter splint is provided, which connects the ureter splint by being turned along with the guide, wherein after releasing this threaded connection the guide can be displaced in the longitudinal direction of the ureter splint in respect to it and, if required, can be completely pulled out. While avoiding a clamped connection as provided by the prior art, and in order for the physician to be able to correctly perform the required rotating movements of the arrangement around its longitudinal axis and in both directions of its longitudinal axis in the course of inserting the ureter splint into the ureter, it is first provided that the guide is in a threaded connection with the auxiliary splint, which forms a rotary connection in both direction of rotation between these two elements and is outside the body of the patient when the ureter splint is inserted, and that the guide can be rotated by a manually operated device in respect to the ureter splint and the auxiliary splint around the common longitudinal axis.

17 Claims, 3 Drawing Sheets

APPARATUS HAVING A URETER SPLINT AND A GUIDE CONNECTABLE TO THE SPLINT VIA A SCREW CONNECTION, AND HAVING AN AUXILIARY SPLINT

BACKGROUND OF THE INVENTION

The invention is based on an apparatus having a ureter splint, a guide, and an auxiliary splint; a detachable screw connection between the guide and the hollow ureter splint is provided, which connects the ureter splint to the guide for coupled rotation. After this screw connection is detached, the guide can be moved in relation to the ureter splint in its longitudinal direction and can be removed entirely. German patent disclosure DE-OS 38 24 244 discloses an apparatus of this kind, in which threads that engage each other are provided on the ureter splint and the guide. The detachment of this screw connection between guide and ureter splint is carried out by a corresponding rotation of the guide relative to the ureter splint. In this case, since practically the entire ureter splint is disposed in the body of the patient, the coupled rotation of the ureter splint is prevented by the engaging of projections of the auxiliary splint in corresponding recesses of the ureter splint. For rotating the guide, a handle is provided on the end of the guide which protrudes from the body of the patient and is oriented toward the doctor. Furthermore, a clamp connection, which must be placed from the outside on the auxiliary splint on its end region oriented toward the doctor, is required to fix the position of ureter splint, auxiliary splint, and guide in relation to one another. A clamp connection of this kind is correspondingly expensive and requires the operation of installing this kind of separate component on the apparatus. It is also difficult to manipulate, because of its weight.

SUMMARY OF THE INVENTION

The stated object of the invention is to embody an apparatus such that by avoiding the aforementioned clamp connection by the doctor during the insertion of the ureter splint into the ureter, the required rotation movements of the apparatus around its longitudinal axis and also in both directions of its longitudinal axis can be executed perfectly. The structural means required for this are more advantageous in structure and operation than the prior art explained above.

To attain this stated object, first it is provided, that the guide and the auxiliary splint are connected with a threaded connection which forms a coupled rotation between these two parts in both rotation directions and is disposed outside the body of the patient when the ureter splint is inserted into the ureter, and that the guide can be rotated in relation to the ureter splint and auxiliary splint around the common longitudinal axis by means of a device to be actuated by hand. With this, during the insertion of the apparatus into the body up to the positioning of the ureter splint in the ureter, it is not necessary to provide for and make use of the separate clamp connection previously in use between guide and auxiliary splint since during this insertion, the threaded connection between guide and auxiliary splint has so much frictional resistance that it transmits rotations at the guide or at the auxiliary splint to the respective other part. After the ureter splint is inserted into the ureter and consequently connects the renal pelvis to the bladder, the guide is rotated relative to the auxiliary splint, which unscrews the threaded connection between guide and ureter splint and thus detaches the guide from the auxiliary splint. Then the guide and the auxiliary splint can be removed. The same is true for a control wire which as a rule is provided and which extends from the end of the apparatus oriented toward the doctor by means of an internal hollow space of a hollow guide provided for this, and through the lumen of the ureter splint into its tip region. In comparison to the aforementioned auxiliary clamps in the form of clamps between auxiliary splint and guide, the apparatus according to the invention is on the one hand structurally simpler and on the other hand is cheaper to produce as a result. In addition, it makes the apparatus easier for the doctor to manipulate. The length of treatment is shortened. It weighs less than the prior clamp connection. This also makes it easier to manipulate. Because of the fact that the external thread of the guide tip is disposed in the inner region of the ureter splint oriented toward the patient, the apparatus according to the invention can be supplied from the factory ready for immediate use. This pre-assembly permits an essential reduction of packaging length. The ureter splint and the other part of the apparatus are situated next to each other in the packaging. This makes it easier to store in the clinic and reduces the manufacture costs of the packaging.

A preferred embodiment of the invention is that the threaded connection between guide 3 and auxiliary splint 2 comprises two threads 21,22 which engage each other and where the auxiliary splint and the guide can be rotated relative to each other around their longitudinal direction (A-B). This makes possible both the above-described common rotation of guide and auxiliary splint around their common longitudinal axis and a rotation of the auxiliary splint relative to the guide around their common longitudinal axis. In addition, the auxiliary splint merely has to be held with one hand and the guide rotated with the other hand. Moreover handles can be provided on the guide and on the auxiliary splint.

Another preferred embodiment of the invention is as follows An additional force for detaching the end of the guide oriented toward the patient from the ureter splint is achieved by the face end of the auxiliary splint oriented toward the patient abutting against the face end of the ureter splint oriented toward the doctor because when the guide is rotated in relation to the auxiliary splint, the threaded contact between these two parts produces a corresponding longitudinal movement of the guide in relation to the auxiliary splint and hence in relation to the ureter splint. The result is a simultaneous rotation of the guide relative to the ureter splint around the common longitudinal axis.

By providing the respective threads with the same screw direction and the same pitch, the unscrewing of the guide from the ureter splint becomes easier. Other advantages and characteristics of the invention can be inferred from the other claims, the description below, and the accompanying drawings of embodiment possibilities of the invention.

DESCRIPTION OF THE PREFERRED EMBODIMENTS

Figure 1:
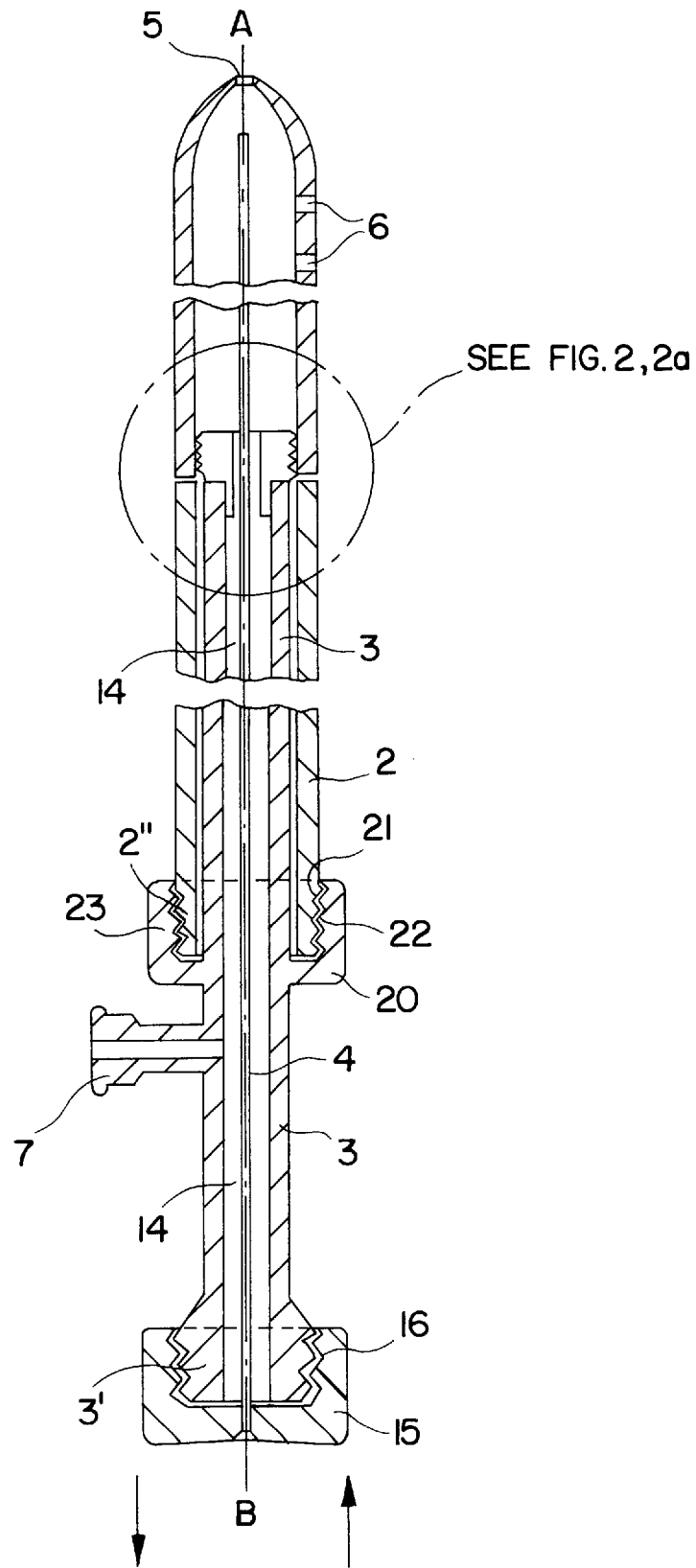
FIG. 1 shows a longitudinal section through an embodiment possibility of the invention.

FIG. 1 shows the components of the exemplary embodiment of an apparatus according to the invention. A ureter splint 1 is provided with an outlet opening 5 on its tip oriented toward the patient and is provided with other outlet openings 6 a little below this tip. In this preferred embodiment of the invention, the face end 1' of the ureter splint 1 oriented toward the doctor either is disposed close to the face end 2' of an auxiliary splint 2 or directly contacts it. A guide 3, which is hollow here and has an enlarged end 3', is disposed inside the auxiliary splint 2. A control wire or internal guide 4 is provided in the lumen 14 of the guide 3, which internal guide is anchored on its end oriented toward the doctor in a syringe fitting 15 which can be screw connected to the enlarged end 3' of the guide 3 by means of a thread 16.

Figure 2:
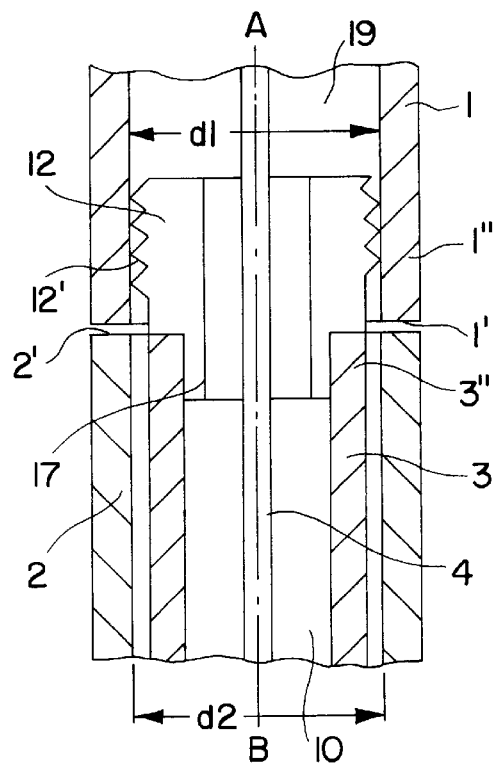
FIG. 2 shows the detail A of FIG. 1 in an enlarged scale.

FIG. 2 shows in detail a threaded connection between the end 3" of the guide 3 oriented toward the patient and the end 1" of the ureter splint 1 oriented toward the doctor. This threaded connection is embodied so that it produces a coupled rotation between guide and ureter splint in both rotation directions. A hard threaded part 12 is firmly connected to the end 3" of the guide 3, which threaded part preferably comprises a metal such as steel and is firmly connected, e.g. glued, to the guide end 3" by means of an annular cylindrical part 17. The threaded part 12 is provided with an external thread 12' which in the embodiment according to FIG. 2 screws with the tip of its thread into the material of the end 1" of the ureter splint, which material in contrast is essentially softer and more elastic. For graphic reasons, this is not shown. Instead of this, an embodiment according to FIG. 2a could also be provided, in which the associated inside of the ureter splint end 1" is provided with an internal thread 18. Here too, the threaded part 12 comprises a hard material (if need be also a correspondingly hard plastic) and the ureter splint end 1" comprises a soft, elastic plastic. Preferably this end 1" is of one piece with the remaining region of the ureter splint 1. In both aforementioned embodiment possibilities, the outer diameter of the thread 12' is somewhat greater than the inner diameter d1 of the ureter splint end 1" (see FIG. 2) or than the inner diameter of the internal thread 18 of the ureter splint end 1" (see FIG. 2a).

Figure 2A:
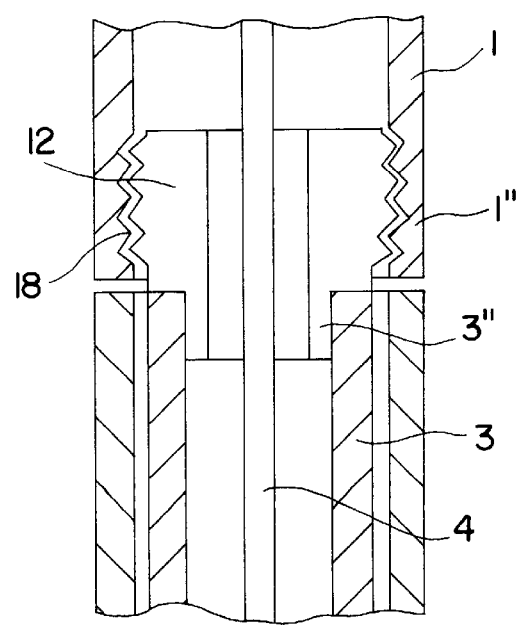
FIG. 2a shows a longitudinal section of a modification of the threaded connection according to FIG. 2.

In both the embodiment according to FIG. 2 and the embodiment according to FIG. 2a, a rotation of the thread 12' in relation to the inner wall of the ureter splint end 1" or in relation to its thread 18 ensues because of the below-described rotation of the guide 3. With corresponding arrangement of the pitch of the thread, this results in a downward movement of the guide 3 with its threaded part 12 relative to the ureter splint 1 (referring to the depiction in the drawing) until the threaded part 12 is situated outside the ureter splint. The pitches of the aforementioned threads 12', 18, and the below-mentioned threads 21, 22 run in the same screw direction. Preferably the pitches of the threads are the same as one another. In addition, it is advised that the diameter d1 of the lumen 19 of the ureter splint is somewhat smaller than the diameter d2 of the lumen of the auxiliary splint 2. This makes entry of the threaded part 12 into the lumen of the auxiliary splint easier.

Figure 3:
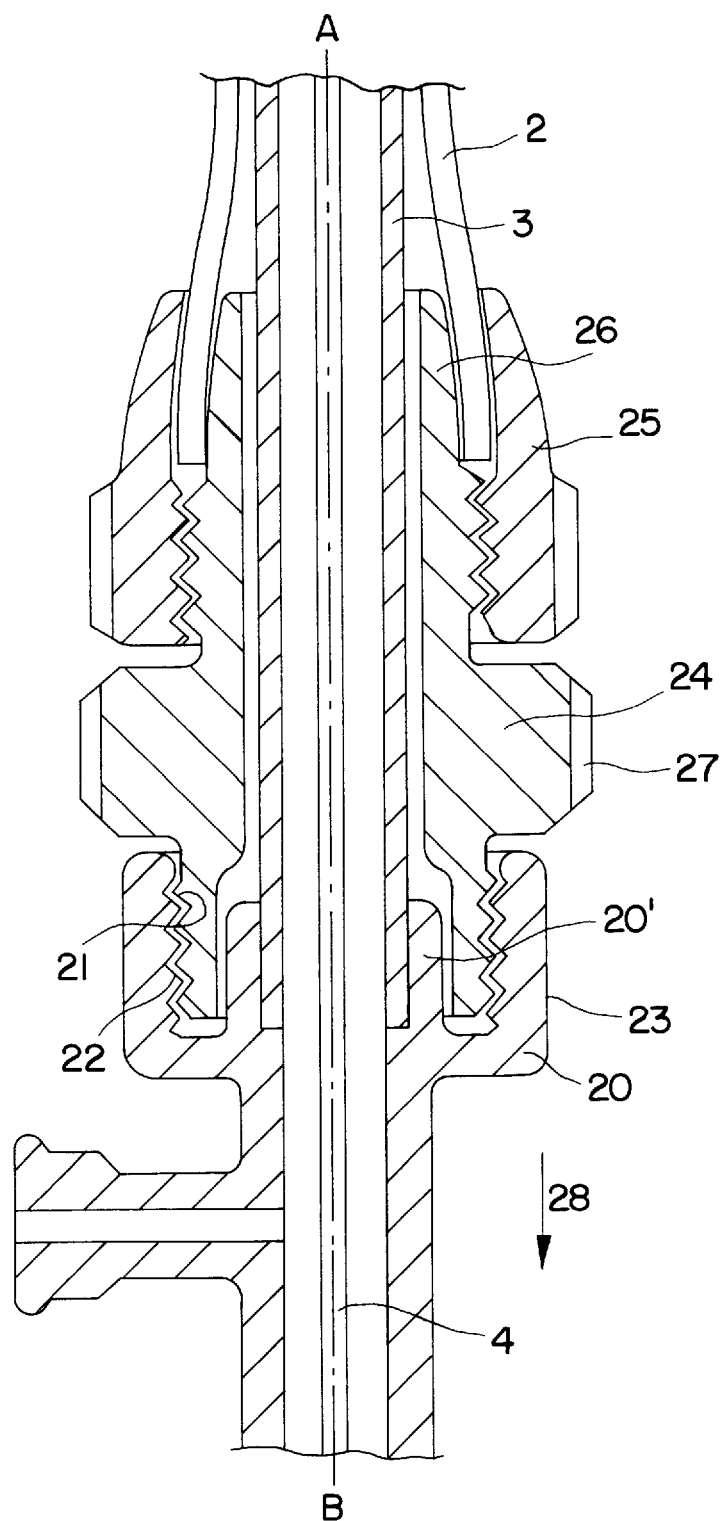
FIG. 3 shows another embodiment possibility of the invention for the threaded connection between guide and auxiliary splint, in a scale which is enlarged in comparison to FIG. 1.

FIG. 1 schematically represents a screw element 20 firmly connected to the guide, which screw element has an internal thread 21, which engages with the external thread 22 on the lower end 2" of the auxiliary splint 2. On its outer surface 23, the screw element 20 is embodied so that it can be grasped there for the purpose of rotating the guide 3 around its longitudinal axis. FIG. 3 shows a preferred embodiment of a connection of this kind. In this exemplary embodiment, the external thread 22 is about as long as the internal thread 21. However, the external thread 22 can also comprise only a few thread turns, in the extreme case it can comprise only one projection with a corresponding pitch, which is disposed on a retaining element 24. The external thread 22 can also be embodied so that a thread of a syringe to be placed there fits over it. This securing element 24 holds the auxiliary splint 2, which is detachably connected by means of a union nut 25 to a projection 26 of the retaining element 24, which projection is on the top in FIG. 3 and is thus on the end oriented toward the patient, and is firmly clamped in the connected position. The retaining element 24 can have laterally protruding, wing-like projections 27, which the user can hold onto between guide 3 and auxiliary splint 2 during the rotation process. One hand firmly holds the auxiliary splint 2 or the retaining element 24 while the other hand rotates the screw element 20 for it around the longitudinal axis A-B of the entire apparatus. With a corresponding aforementioned arrangement and embodiment of the pitches of the threads 21, 22, the screw element 20 moves downward in the direction of the arrow 28, i.e. toward the doctor. This and the simultaneous rotation of the threaded part 12, which is embodied to fit in terms of its pitch, in relation to the ureter splint end 1" produces a downward movement of the guide 3 when the guide 3 and threaded part 12 are simultaneously rotated around the longitudinal axis A-B of the apparatus. At the same time, this achieves the detachment of the end of the guide oriented toward the patient from the ureter splint.

It can be inferred in particular from FIG. 3 that when both elements 20, 24 are rotated in relation to each other, a corresponding rotation of the auxiliary splint 2 in relation to the guide 3 is also produced, wherein the parts 2, 25, and 24 constitute a functionally connected component. The same is true for the parts 20 and 3, which are firmly connected, e.g. glued, to each other via a fitting 20'.

The apparatus according to the invention can be supplied from the factory in the form shown in FIG. 1, in which it is ready to be inserted into the body of the patient. Otherwise the doctor assembles the parts, according to instructions, in the connecting position according to FIG. 1. The close opposition or abutment of the face end 1' of the ureter splint and face end 2' of the auxiliary splint achieves two advantages. Since the outer diameter of the ureter splint and auxiliary splint can be chosen to be the same as each other, consequently no edge of the face end of the auxiliary splint or of the face end of the ureter splint protrudes, which could lead to injuries when inserting the apparatus into the body of the patient or when pulling it back and forth there. In addition, when the internal thread 21 of the screw element 20 is rotated in relation to the external thread 22 of the retaining element 24 of the auxiliary splint 2, this forms an abutment on the face end 1' of the ureter splint, which supports the movement of the screw element 20 with the guide 3 in the direction of the arrow 28. The aforementioned contact of the two face ends 1', 2' with each other can be achieved by correspondingly matching the length of the auxiliary splint to the position of the screw element 20 on the guide 3 (provided that this is screwed with its threaded part 12 into the ureter splint).

If the ureter splint is disposed in the required position in the ureter, then the tip of the control wire 4 is pulled back into the ureter splint. This position is also secured by the fastening or screw connection of a control wire 4 of this kind to the syringe fitting 15, which is screwed to the enlarged end 3' of outer guide. After detaching this screw connection, the inner part of the guide or control wire 4 can be pulled downward out of the ureter splint and the guide with the aid of the syringe fitting 15. Then the decoupling of the other parts, namely outer part of the guide 3 and auxiliary splint 2 from the ureter splint, can be carried out by detaching the above-explained screw connections 12', 1", and 21/22.

The apparatus according to the invention furthermore allows the supply of a radiographic contrast medium via the lumen 10 of the outer part of the guide 3 and the lumen 19 of the ureter splint 1. The radiographic contrast medium can be introduced into the renal pelvis by means of the opening 5 in the tip of the ureter splint. If there is no opening of this kind, then lateral openings 6 of the ureter splint can also be used for this. This takes place before the decoupling of the aforementioned parts of the apparatus. The supply of the radiographic contrast medium can be carried out either by means of a fitting 7 or by means of a corresponding hose connection, which leads into the lumen 14 of the guide 3 on its end in a location which can be accessed on the end oriented toward the doctor. It would also be possible to supply a radiographic contrast medium by means of the outlet of the lumen 8 in the region of the enlargement 3', which outlet is oriented toward the doctor. In this case, the syringe fitting 15 together with the control wire 4 would have to have been previously removed.

Instead of the control wire 4 which, in the embodiment according to FIG. 1, is used to compensate for the so-called "Memory", a correspondingly thin inner guide can also be provided. The outer guide 3, though, does not change in its embodiment or function. A thin inner guide of this kind can have a soft tip so that it does not injure the body of the patient even when protruding out of the opening 5 of the ureter splint. In another embodiment of an inner guide, this can be sturdy so that it can compensate for a remaining curvature (so-called "Memory") of the ureter splint tip given to it in the factory.

Furthermore, the invention permits the use of a double guide in which the inner guide has a stiffened tip, which produces the aforementioned "Memory". In this case, the outer guide is also embodied according to the invention.

If a control wire or an inner guide is to be slid out of the ureter splint tip, then the already-explained opening 5 must be provided for this. An apparatus can also be used with which the inner guide is a relatively stiff, hollow control wire in which another control wire is disposed, which is thin and soft, and can additionally be moved in the longitudinal direction. A hollow control wire can also be provided, which has a "Memory" on the end oriented toward the patient and in whose interior, a stiffening wire is disposed.

All features shown and described, as well as their combination with one another, are essential to the invention.

What is claimed is:

1. An apparatus comprising a hollow ureter splint (1), a hollow guide (3) having an upper part and a tip, and a hollow auxiliary splint (2) having an upper part and an end part, wherein the auxiliary splint (2) sheathes the guide (3) between the upper part and the tip, which further comprises i) a detachable threaded connection between the tip of said guide (3) and one end of said ureter splint (1), thereby allowing for
a) coupled rotation of the guide (3) and the ureter splint (1) around their common axis, and
b) movement of the guide (3) in a longitudinal direction relative to the axis of the guide upon detachment of its connection to the ureter splint (1);

ii) a threaded connection between the upper part of the auxiliary splint (2) and the guide (3) which allows a coupled rotation of said guide and said auxiliary splint around their common axis.

2. The apparatus of claim 1, wherein the detachable threaded connection between the guide (3) and the ureter splint (1) is embodied for coupled rotation in both rotation directions.

3. The apparatus of claim 1, wherein the tip (12) of the guide oriented toward the patient has an external thread (12') made of a hard material and is disposed in or can be inserted into the inside of the end (1") of the ureter splint (3) oriented toward the doctor, which end, in contrast, comprises a softer, and more elastic material, wherein the outer diameter of the external thread (12') of the guide tip (12) is somewhat larger than the inner diameter of the region of the ureter splint contacting it.

4. The apparatus of claim 1, wherein the threaded connection between guide (3) and auxiliary splint (2) comprises two threads (21, 22) which engage each other, wherein the auxiliary splint and the guide can be rotated relative to each other around their longitudinal direction (A-B).

5. The apparatus of claim 4, wherein the thread (21) of the guide (3) is disposed on a screw element (20) which is externally embodied or suited to be grasped by hand and has the thread (21) on the inside, wherein the screw element (20) is firmly connected to the guide.

6. The apparatus of claim 5, wherein the screw element, having an internal bore and a hollow fitting (20') affiliated with it, is glued to the outside of the guide (3).

7. The apparatus of claim 4, wherein the end of the auxiliary splint oriented toward the doctor is attached to a retaining element (24) whose thread (22) engages the thread (21) of the screw element (20) and which, together with the auxiliary splint (2), can be rotated in relation to the guide (3) around the longitudinal axis (A-B).

8. The apparatus of to claim 5, wherein the thread (21) of the screw element (20) is embodied as an internal thread and the thread (22) of the retaining element (24) is embodied as an external thread engaging it and that the external thread (22) either extends over the entire length of the internal thread (21) or extends over a partial region only.

9. The apparatus of to claim 8, wherein the external thread (22) of the retaining element (24) comprises only a few thread turns which extend from the face end of the retaining element and preferably are embodied so that they fit the thread of a syringe to be fastened to the retaining element.

10. The apparatus of to claim 5, wherein the retaining element (24) is provided with handles which protrude outward, e.g. in the shape of wings (27).

11. The apparatus of to claim 5, wherein the end of the auxiliary splint (2) oriented toward the doctor is firmly but detachably connected to the retaining element (24) by means of a union nut (25).

12. The apparatus of to claim 1, wherein the length of the auxiliary splint (2) and the position of its threaded connection (21/22) with the guide (3) are matched to each other so that when the apparatus is ready to insert, the face end (1') of the ureter splint (1) oriented toward the doctor and the face end (2') of the auxiliary splint (2) oriented toward the patient contact one another or closely oppose each other.

13. The apparatus of to claim 1, wherein the threaded part (12, 12') on the tip of the guide (3) is a separate component

(12) with an external thread (12') which is firmly connected to the end (3") of the guide (3) oriented toward the patient.

14. The apparatus of to claim 13, wherein the threaded part (12) comprises a hard metal, e.g. steel.

15. The apparatus of to claim 1, wherein the inside of the end (1") of the ureter splint (1) oriented toward the doctor has an internal thread (18) which fits the external thread (12') of the guide tip.

16. The apparatus of to claim 1, wherein the respective threads (12, 12'; 18; 21, 22) have the same screw direction and the same pitch.

17. The apparatus of claim 15, wherein the internal thread (18) of the end (1") of the ureter splint (1) oriented toward the doctor is disposed on a separate part which is firmly installed on the inside of the end oriented toward the doctor.

* * * * *

UNITED STATES PATENT AND TRADEMARK OFFICE
CERTIFICATE OF CORRECTION

PATENT NO.:  5,817,122

DATED:  October 6, 1998

INVENTOR(S):  Hans E. SACHSE

It is certified that error appears in the above-identified patent and that said Letters Patent is hereby corrected as shown below:

On the title page, Item [57],

In the abstract, line 1, delete "split" and substitute --splint--.

In the abstract, line 5 from the bottom, "direction" should be --directions--.

Signed and Sealed this

Twenty-seventh Day of July, 1999

Attest:

Attesting Officer

Q. TODD DICKINSON

Acting Commissioner of Patents and Trademarks